United States Patent
Buff

[11] Patent Number: 5,496,278
[45] Date of Patent: Mar. 5, 1996

[54] SAFETY SYRINGE WITH SELF-SEALING NEEDLE RETRACTION AND RETRACTED MEMBER LOCK

[76] Inventor: Danny Buff, Rte. 4 Box 996 A, Marion, N.C. 28752

[21] Appl. No.: 285,909

[22] Filed: Jul. 25, 1994

[51] Int. Cl.$^6$ ................................................. A61M 5/00
[52] U.S. Cl. ........................ 604/110; 604/195; 604/220
[58] Field of Search ............................ 604/110, 187, 604/192, 218, 220, 263, 195

[56] References Cited

U.S. PATENT DOCUMENTS

| | | | |
|---|---|---|---|
| 4,728,321 | 3/1988 | Chen | 604/110 |
| 4,820,272 | 4/1989 | Palmer | 604/220 X |
| 4,995,869 | 2/1991 | McCarthy | 604/110 |
| 5,045,063 | 9/1991 | Spielberg | 604/218 X |
| 5,106,372 | 4/1992 | Ranford | 604/220 X |

*Primary Examiner*—John D. Yasko
*Attorney, Agent, or Firm*—John D. Gugliotta

[57] ABSTRACT

A safety syringe includes a means for retracting a used needle within the syringe, sealing the syringe and locking the plunger in a retracted position requiring only conventional syringe manipulation. Accidental contact with a used needle or syringe contents is thereby prevented such that the syringe can be safely discarded in a conventional manner. A needle clamp augmentation to the front surface of the syringe plunger is engageable with the needle head portion of a hollow needle releasingly mounted to the syringe. A sealant cavity formed proximate to the needle end of the syringe contains a sealing compound. A sealant cavity cover prevents migration of the sealing compound into the syringe cylinder. Fully depressing the plunger causes the needle clamp to engage the needle head portion. Retracting the plunger dislodges and retracts the needle, drawing a sealing means about the gap left by the retracted needle and preventing fluid leakage. A locking clamp preferably extending from the inner surface of the syringe engages a sufficiently retracted plunger thereby preventing subsequent plunger depression.

10 Claims, 4 Drawing Sheets

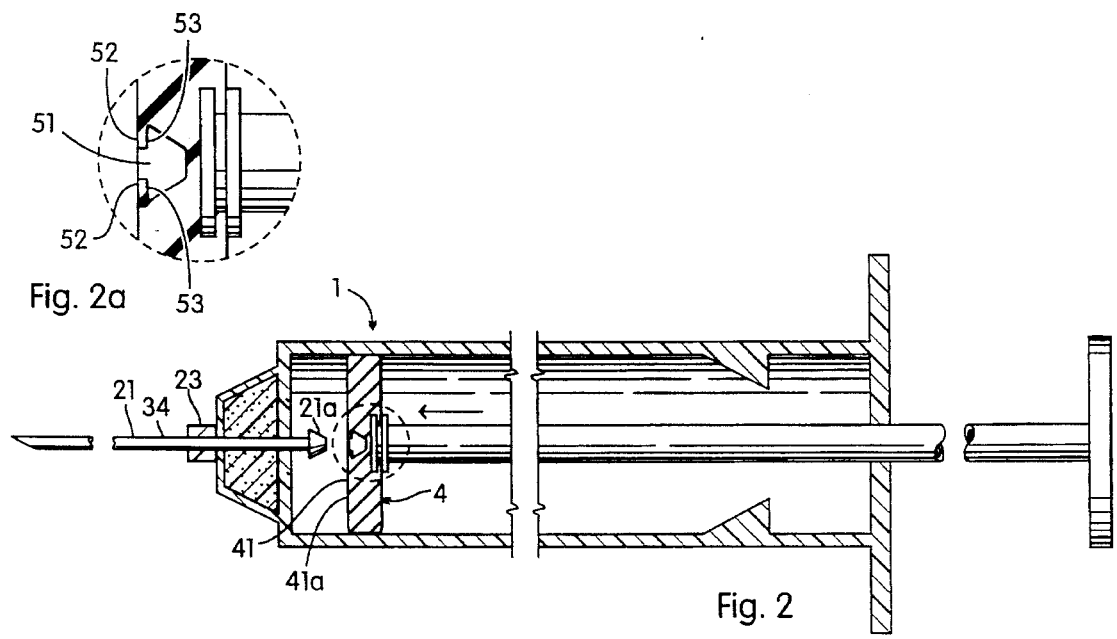
Fig. 2a
Fig. 2
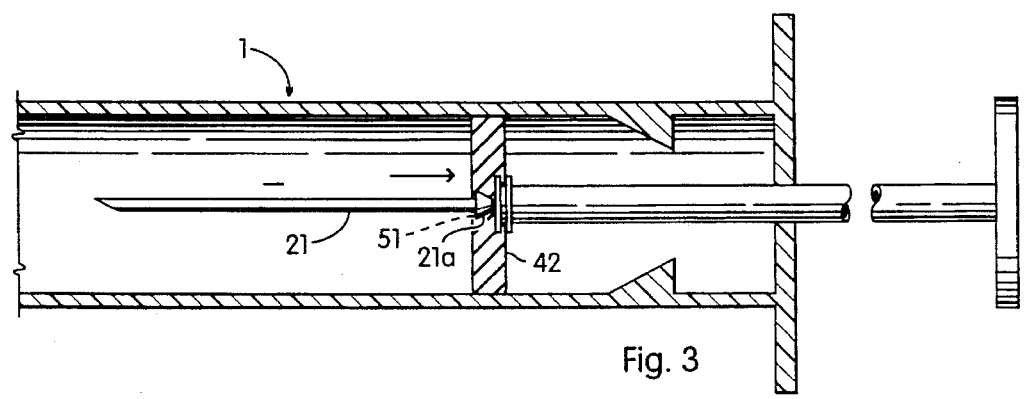
Fig. 3

SAFETY SYRINGE WITH SELF-SEALING NEEDLE RETRACTION AND RETRACTED MEMBER LOCK

BACKGROUND OF THE INVENTION

1. Field of Invention

This invention relates generally to syringes, and more particularly, to syringe assemblies wherein unintentional exposure is preempted utilizing permanent needle retraction and cylinder sealing.

2. Description of Prior Art

The simple sealed cylinder, permanently-affixed needle and movable plunger arrangement of a conventional syringe provides a number of desirable qualities. In addition to reliability and low cost, the tube is gripped, the needle maneuvered and the plunger depressed utilizing a single, well established and non-distracting one-handed motion. Such operation is critical in the often frantic health care environment. However, used syringes pose a serious health risk due to: (1) scraping or pricking of the skin by an exposed needle; (2) accidental secondary injection (3) ingestion or often even mere contact with residual chemicals and/or bodily fluids escaping from a discarded syringe. Disposal of syringes therefore extends the risk beyond the health care environment.

Simple screening type solutions, while retaining the simple syringe mechanism, are plagued with inherent problems. Needle caps are subject to loss, improper affixing and dislodging. Syringe disposal containers add inordinate expense. In addition, both introduce additional attention-diverting, unfamiliar, two-handed manipulation into a time/procedure critical environment.

Attention has therefore shifted to modifying the syringe mechanism itself; more specifically, to safety syringes wherein, following syringe use, an augmented plunger dislodges the needle which is then drawn into the cylinder. Hailer, U.S. Pat. No. 4,026,287 (snap-fit and screwable plunger-to-needle head interfaces), McGary, U.S. Pat. No. 5,053,010, Bin, U.S. Pat. No. 4,955,869 and Terrill, U.S. Pat. No. 4,978,340 (pressure fit plunger to needle head or head assembly interfaces), Haber, U.S. Pat. No. 4,908,022 (suction cup interface), Chen, U.S. Pat. No. 5,242,402 (needle angularly engaged), DeChellis, U.S. Pat. No. 4,921,486 (dislodge interface and needle spring mechanism), Wallingford, U.S. Pat. No. 5,098,390 (reusable needle).

One disadvantage of these assemblies is that the needle remains subject to further depression of the plunger, thereby again potentially exposing the needle. Proposed solutions either fail to solve this problem or create further problems. The angular needle retraction proposed by Chen remains subject to foreseeable pressure on the plunger, as does the "floating" catapulted needle of DeChellis. A perforated, breakaway plunger "handle" proposed by Haber et al, U.S. Pat. No. 4,826,484, presents reliability questions during use and requires unconventional manipulation and disposal. Utilizing the threaded plunger-to-cylinder-cavity locking mechanism disclosed by Harris, U.S. Pat. No. 5,222,944, similarly requires added manipulation that is distracting to immediate life-saving concerns.

A second disadvantage is the complexity of the proposed mechanisms, which necessarily increases cost, compromises reliability and may well impede acceptance by practitioners.

A third disadvantage is that these assemblies fail to address the problem of sealing the cavity that remains after the needle is retracted. The singular, molded plug mechanism posed by Chen is complex, subject to failure and adds considerable expense to syringe manufacture. In addition, offset needle positioning for special applications denies sufficient space for such a method.

Thus there is a need for a safety syringe that reliably and inexpensively retracts the needle, assures that the needle will remain retracted and seals the needle cavity following syringe use; a safety syringe that further accomplishes these goals through user manipulation commensurate with that required for a conventional syringe.

SUMMARY OF THE INVENTION

The present invention, while providing a practical needle retraction means, further provides practical means for sealing the cavity formerly occupied by the needle and for locking the retracted needle in place that can be used with this and other needle retraction means. Needle retraction is accomplished by augmenting the needle and plunger heads such that the plunger locks in a pressure fit manner to the needle during conventional use. The needle cavity is sealed through the use of a specially designed sealant cavity containing sealant material at the needle end of the cylinder; thus operation is automatic and independent of both needle positioning and the needle retraction means utilized. Locking the retracted needle within the cylinder is accomplished by augmenting the inner surface of the cylinder with a needle or plunger head accepting clamp; thus only minimal, non-distracting one-handed operation is required and, once again, needle position and retraction means are inconsequential. In addition, a minimum of perforations can be added to the exposed end of the plunger for removing the plunger end without compromising reliability.

One object of the invention is therefore to provide a safety syringe that utilizes a needle retraction method for automatically engaging and retracting the needle following use.

A second object of the invention is to provide a means for retaining the needle in a retracted position that is intuitive and requires only minimal, non-distracting, one handed operation.

A third object of the invention is to provide such a syringe wherein fluid within the syringe cannot escape through the cavity formerly occupied by the retracted needle.

A fourth object of the invention is to provide retaining and sealing means that are essentially independent of needle positioning and needle retraction means utilized and that further provides for practical implementation of plunger shaft removal and other supplemental protection means.

These and other objects, advantages, features and benefits of the present invention will become apparent from the drawings and specification that follow.

BRIEF DESCRIPTION OF THE DRAWINGS

FIG. 2 is a partial schematic, longitudinal cross-sectional view thereof, showing how the plunger defines an integral needle head clamp engageable with the needle head merely by depressing the plunger as with a conventional syringe.

FIG. 2a is an enlarged view taken from FIG. 2 and showing further detail of the needle head clamp.

FIG. 3 is a partial schematic, longitudinal cross-sectional view thereof showing how conventional plunger retraction acts to dislodge and retract the now engaged needle.

DETAILED DESCRIPTION OF THE PREFERRED EMBODIMENT

Figure 1:
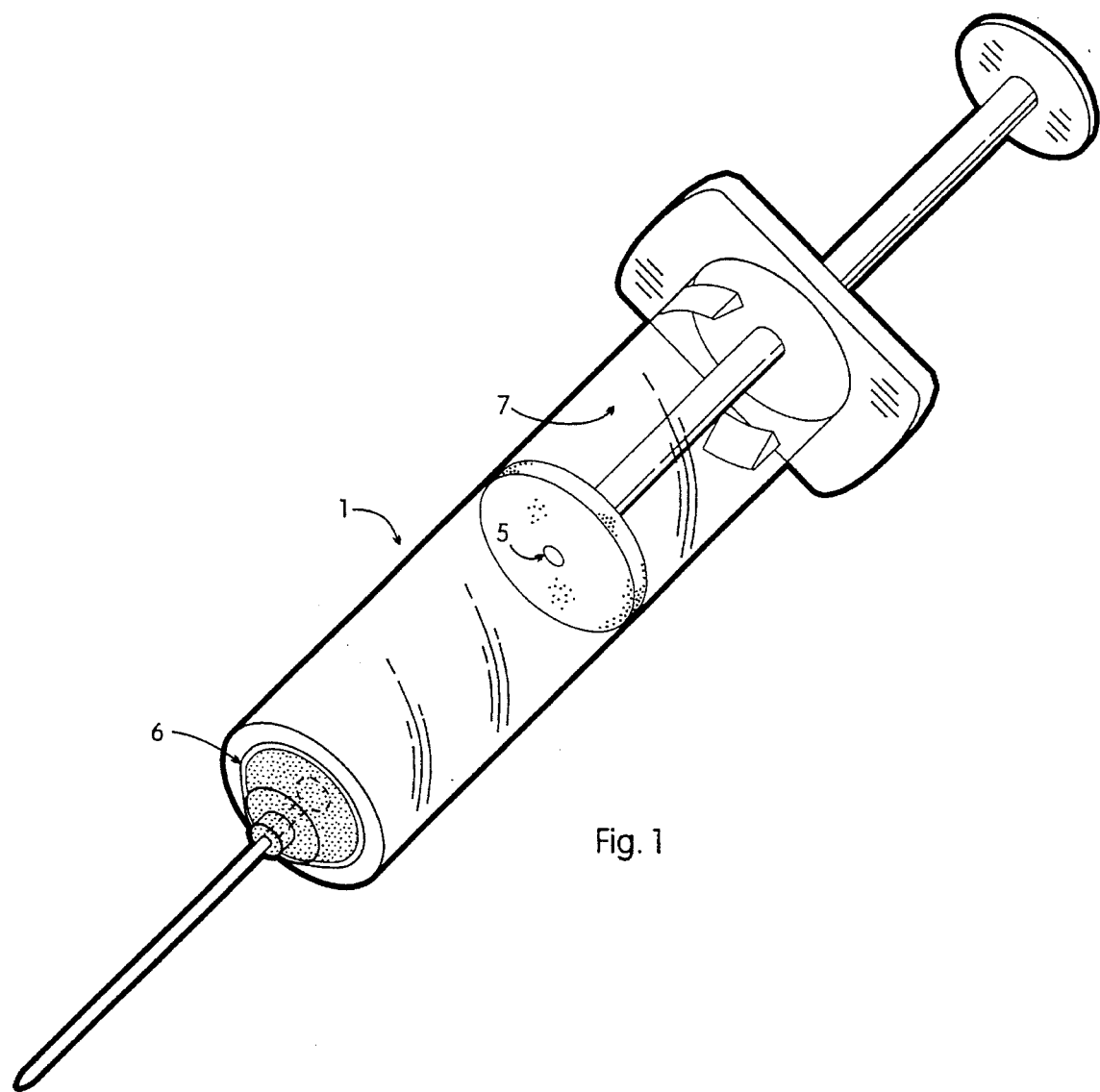
FIG. 1 is a bottom perspective view of the Safety Syringe With Self-Sealing Needle Retraction And Retracted Member Lock, showing how the needle retraction, sealing and locking means are preferably contained within a conventional syringe housing.

FIG. 1 shows that the Safety Syringe With Self-Sealing Needle Retraction And Retracted Member Lock (Syringe) 1 provides needle retraction means 5, needle cavity sealing means 6 and needle retraction locking means 7 within a conventional syringe configuration. Thus while the risk of contact with an exposed needle or escaping fluid from a used syringe are essentially removed, practitioner familiarity and conventional syringe packaging, disposal, etc. are not compromised.

FIGS. 2 through 3 show that the needle retraction means 5 comprises augmenting the needle side 41a of the plunger head 41 with a flexible recess shaped as a needle head clamp 51 that is engageable with the needle head 21a. To ensure reliability, the shape of the needle head clamp 51 is commensurate with that of a conventional barrel type clamp and the bottom surface of the needle head 21a is preferably flattened. Thus ordinary depression of the plunger 4 easily forces the needle head 21a through the flexible angular jaws 52 of the flexible needle head clamp 51; recoiling the angular jaws 52 securingly engaging the needle head 21a on the clamp shelves 53. Once so engaged, withdrawing the exposed plunger end 42 retracts the needle 21 into the syringe cylinder portion 32 of the syringe 1. A needle securing ring 23 affixed to the outer surface of the needle end 34 of the cylinder 3 adds further stability by securing the needle 21 during Syringe 1 use, as with conventional syringes.

Figure 4:
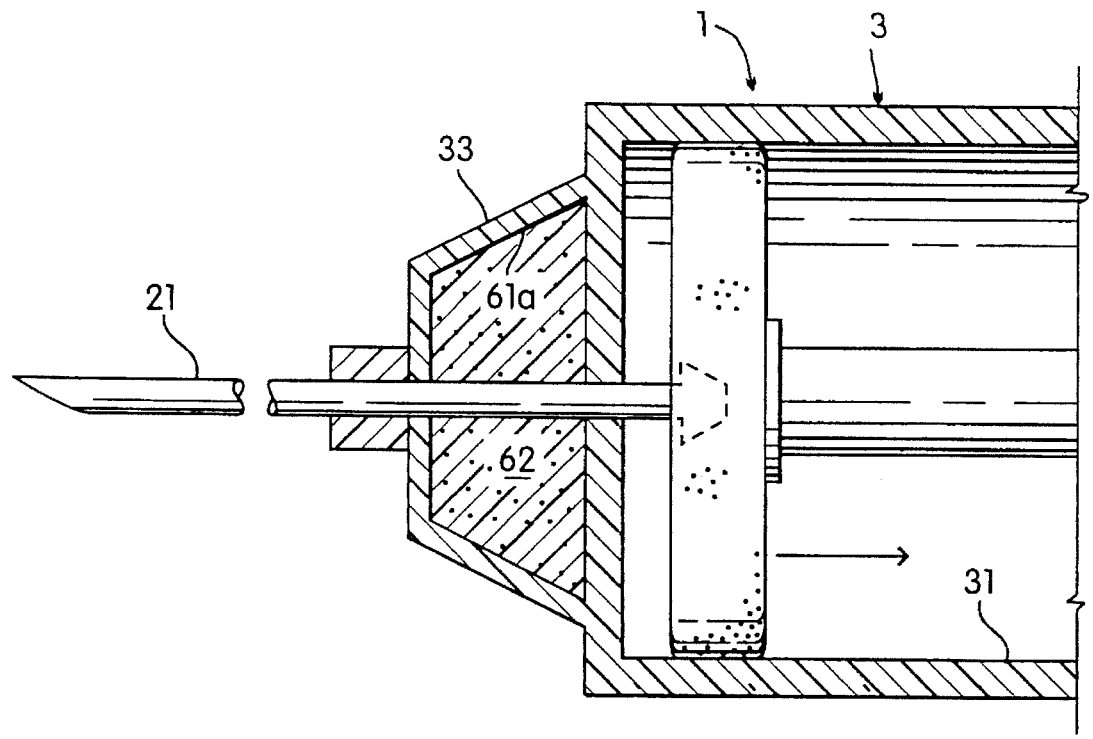
FIG. 4 is a cross-sectional view thereof, showing how an integral cover and the inner surface of the syringe define a cavity essentially filled with a conventional non-toxic, fluid repelling resin.
Figure 5:
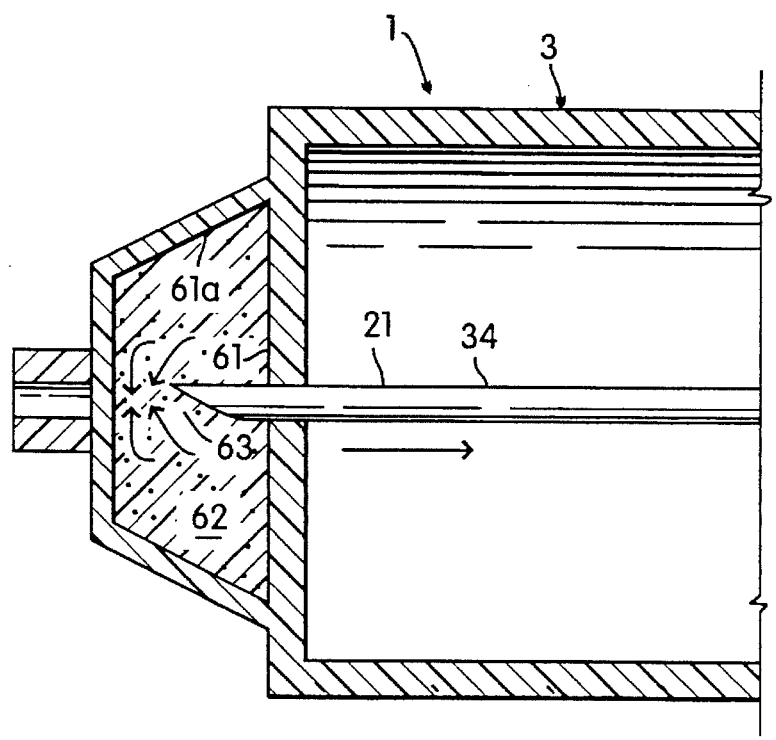
FIG. 5 is a cross-sectional view, showing how the resin is drawn into the needle cavity formed by the retracting needle due the pressure created by the retracting needle, thereby sealing the cavity and preventing fluid from escaping from the syringe cylinder.

FIGS. 4 and 5 show that the inner surface 31 of the cylinder 3 forms a integral sealant cavity 61a containing a conventional non-toxic, fluid-repelling, resin compound type sealant 62 at the tapered end portion 33 of the cylinder 3. Thus pressure caused by retraction of the needle 21 into the cylinder 3 draws the sealant 62 into the needle cavity 63 remaining as the needle 21 is retracted. A molded cavity cover 61 ensures that the sealant 62 remains in the sealant cavity 61a for optimal sealing and to preempt the possibility of contamination of syringe cylinder portion 32 contents during Syringe 1 use.

Figure 6A:
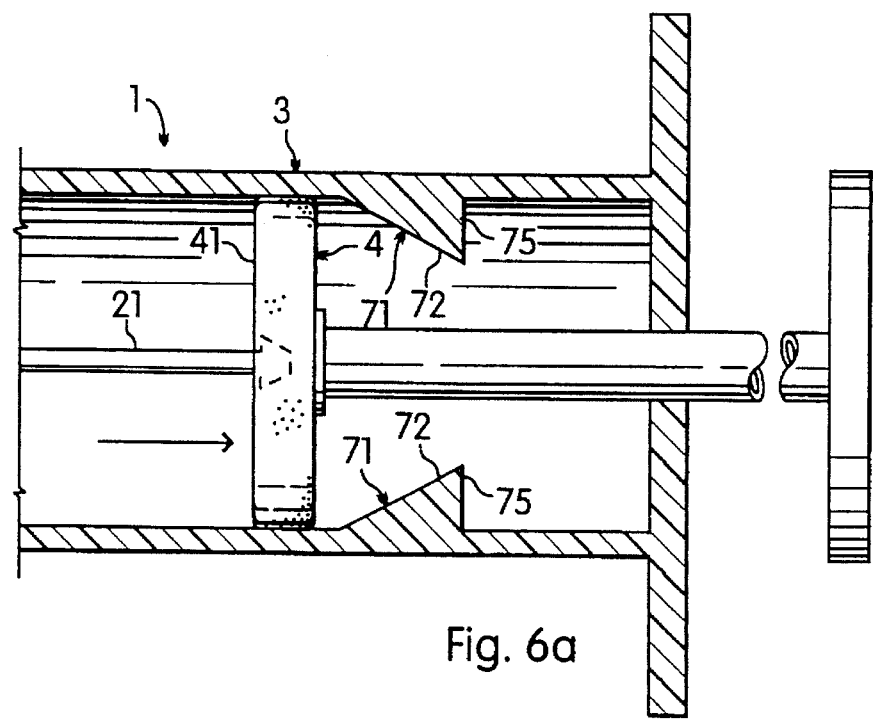
FIGS. 6a is a cross-sectional view, showing how conventional retraction of the plunger draws the plunger and an engaged needle toward a plurality of integral locking clamps.
Figure 6B:
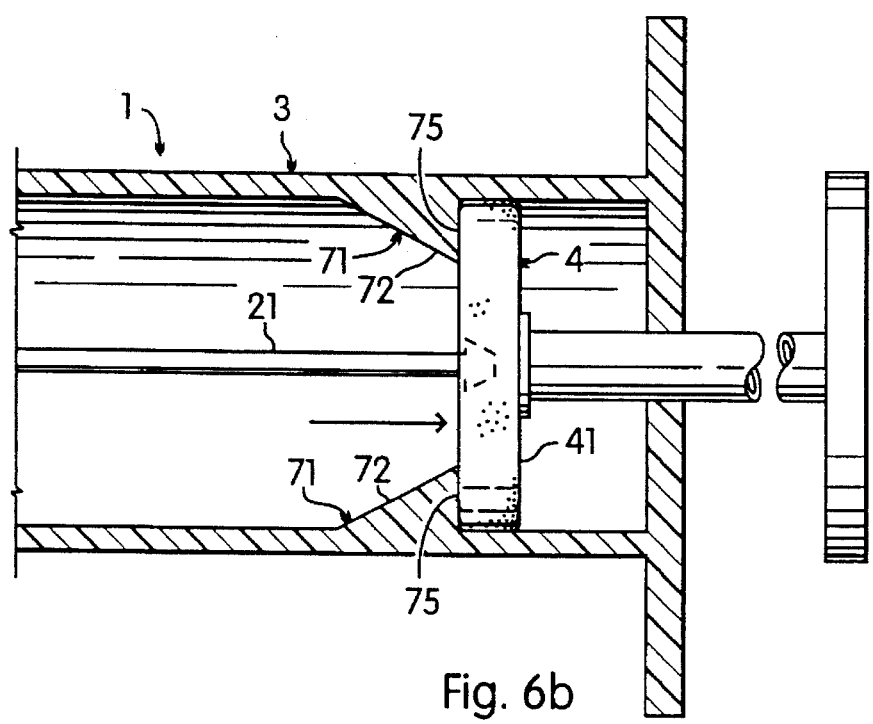
FIG. 6b is a cross-sectional view as in FIG. 6, showing how further conventional retraction of the plunger engages the plunger with the locking clamps, thereby preventing the plunger from subsequent depression and the now fully engulfed needle from subsequent extension from the syringe.

FIGS. 6a and 6b show that the retracted needle 21 and plunger head 41 combination is retained in a retracted position through the use of a locking clamp 71 augmentation to the inner surface of the cylinder 3 proximate to the cylinder end opposite the unretracted needle 21. Once again, the locking clamp 71 design is preferably commensurate with that of a conventional barrel clamp; the locking clamp 71 is simply sized to be securingly engageable with the plunger head 41. In addition to providing a simple, inexpensive and reliable locking means, no further manipulation is required to lock the retracted needle 21 in place other than to sufficiently withdraw the plunger 4.

While the above description contains many specificities, these should not be construed as limitations on the scope of the invention, but rather as an example of the preferred embodiment thereof. Many other variations are possible within the spirit and scope of the present invention.

For example, the locking clamp of the present invention can be used to add permanency to other needle retraction means. While a barrel type clamp is preferred as an optimally reliable design, numerous shapes can be employed so long as the locking clamp is sized and shaped to effectively engage the plunger head, a needle head augmentation or both.

A second example is that the shape and plastic composition of the locking clamp can be varied in numerous ways without affecting needle locking reliability; rubber composition is just one example. In addition, the locking clamp can be molded as one or more components affixed to the inner cylinder surface or a plurality of grooves defined by the inner cylinder surface in addition to the integral clamp of the preferred embodiment. Further, the needle head clamp and locking clamp, while preferably formed as described above, can be effectively formed as recesses, surface augmentations and/or appendages.

A third example is that the sealant cavity and sealant can also be utilized with other needle retraction methods in a non-interfering manner. A plurality of gaskets can further be affixed within the sealant cavity and/or within the remaining cylinder cavity to further prevent fluid contamination by the sealant itself. In addition, the sides of the sealant cavity cover abutting the needle can be formed to recoil as the needle is retracted, thereby providing improved sealing capability; such recoiling, however, was not preferred due to added resistance to plunger movement.

A fourth example is that needle placement along the central longitudinal axis is utilized only for illustrative purposes. Shifted axial needle placement for specific medical procedure applications is readily accommodated by the present invention through a simple re-alignment of the respective cavities, clamps and cylinder size and shape. Such permutations merely demonstrate the anticipated adaptability advantages of the present invention over prior art.

A fifth example is that the needle need only be retracted to the extent that it no longer protrudes from the syringe and the sealing compound acts to effectively seal the syringe. Lesser needle retraction than that of the preferred embodiment advantageously requires lesser user manipulation. However, engulfment of the needle within the syringe cylinder is thought to preclude failure of the sealant due to needle-sealant interaction considering available sealing compounds and the variety of potential disposal site conditions.

There are, of course, other anticipated embodiments also within the spirit and scope of the present invention.

I claim:

1. A safety syringe with self-sealing needle retraction and retracted member lock comprising:

a syringe cylinder having a plunger end, a needle end, an outer surface and an inner surface, also having an integral cylinder portion extending from the plunger end to a cover point and an integral tapered portion extending from the cover point to the needle end, the needle end of the syringe cylinder defining a syringe needle slot for aligning a partially inserted needle along a longitudinal axis within the syringe cylinder;

a securing ring affixed to the needle end of the syringe cylinder, the securing ring defining a ring needle slot sized and aligned commensurate with the syringe needle slot for releasingly securing and aligning a partially inserted needle along a longitudinal axis within the syringe cylinder;

a tubular needle means for transferring fluids between a patient and the syringe cylinder comprising an integral shank abutting an integral enlarged needle head, the needle means being partially inserted into the syringe cylinder such that the needle head extends within the cylinder portion of the syringe cylinder and the shank extends outwardly from the securing ring, to which the needle means is releasingly affixed, during such transfer of fluid;

a plunger reciproactively held in the syringe cylinder for boosting a fluid medicine in the syringe cylinder to be injected into and drawing fluid from a patient through the needle means, the plunger having a front surface, the front surface defining a needle clamp securingly engageable with the needle head such that full depression of the plunger causes such engagement and subsequent retraction of the plunger further causes dislodging and retraction of the needle means;

a locking clamp affixed proximate to the plunger end of the inner surface of the cylinder portion of the syringe cylinder for engaging and restraining a sufficiently retracted plunger from subsequent depression; and a sealing means comprising a cover shaped to essentially conform with the front surface of the plunger and secured about its circumference to the inner surface of the syringe cylinder proximate to the cover point, the cover and the inner surface of the tapered portion of the syringe cylinder defining a sealant cavity containing a conventional liquid repelling sealing compound, the cover further defining a cover needle slot sized and aligned commensurate with the syringe needle slot, such that the sealing compound is drawn into a needle cavity defined by a retracting needle while mixture of the sealing compound with fluid within the syringe cylinder is prevented.

2. The safety syringe with self-sealing needle retraction and retracted member lock as defined in claim 1 wherein the needle means extends along the center longitudinal axis of the syringe cylinder.

3. The safety syringe with self-sealing needle retraction and retracted member lock as defined in claim 1, wherein the needle head of the needle means has an essentially flat lower surface extending transversely from the shank of the needle means such that the plunger is more reliably engageable with the needle means.

4. The safety syringe with self-sealing needle retraction and retracted member lock as defined in claim 1, wherein the needle clamp defined by the front surface of the plunger comprises a plurality of flexible jaws and shelves, such that full depression of the plunger forces the needle head through the jaws of the needle clamp, thereby securing the needle head on the shelves.

5. The safety syringe with self-sealing needle retraction and retracted member lock as defined in claims 1 or 4, wherein the needle clamp of the front surface of the plunger is defined by an outwardly extending augmentation of the front surface of the plunger.

6. The safety syringe with self-sealing needle retraction and retracted member lock as defined in claim 1, wherein the locking clamp comprises a plurality of clamping means protruding from the inner surface of the syringe cylinder.

7. The safety syringe with self-sealing needle retraction and retracted member lock as defined in claim 1 or claim 6, wherein the locking clamp has a plurality of flexible angular jaws and locking shelves for providing more reliable retracted plunger locking as with a conventional barrel type clamp.

8. The safety syringe with self-sealing needle retraction and retracted member lock as defined in claim 1, wherein the locking clamp comprises a plurality of slot type recesses defined by the inner surface of the syringe cylinder.

9. The safety syringe with self-sealing needle retraction and retracted member lock as defined in claim 1, wherein the cover needle slot defined by the cover of the sealing means is shaped as an elongated tube for more reliably preventing the sealing compound from mixing with and thereby contaminating fluid in the cylinder of the syringe cylinder.

10. A method of sealing fluid contained in a cylinder portion of a syringe cylinder as a retractable needle is retracted into the syringe cylinder, said method comprising the steps of: (a) forming a sealing cavity proximate to a needle end of the syringe cylinder; (b) extending and releasingly securing needle means through said sealing cavity along a longitudinal axis of the syringe cylinder; and (c) substantially filling the sealing cavity with a sealing compound, thereby sealing said cavity and preventing escape of the fluid contained in the cylinder portion after the retractable needle is removed from the sealing cavity.

* * * * *